United States Patent [19]

Anderson et al.

[11] 4,220,792
[45] Sep. 2, 1980

[54] 1-PHENYL-PYRAZOLE DERIVATIVES

[75] Inventors: Paul L. Anderson, Dover; Nicholas A. Paolella, Livingston, both of N.J.

[73] Assignee: Sandoz, Inc., E. Hanover, N.J.

[21] Appl. No.: 6,462

[22] Filed: Jan. 25, 1979

[51] Int. Cl.$^2$ .................................. C07D 231/14
[52] U.S. Cl. ............................ 548/378; 424/273 P
[58] Field of Search ................................. 548/378

[56] References Cited

U.S. PATENT DOCUMENTS

| | | | |
|---|---|---|---|
| 3,254,093 | 5/1966 | Huisgen et al. | 548/378 |
| 3,752,818 | 8/1973 | Plumpe et al. | 548/378 |

OTHER PUBLICATIONS

Takamizawa et al., Chem. Abst. 1960, vol. 54, p. 14272a.
Takamizawa et al., Chem. Abst. 1959, vol. 53, p. 16115f.
Takamizawa et al., Chem. Abst. 1963, vol. 59, p. 10023a.
Finar et al., J. Chem. Soc. 1959, p. 1819–1823.

*Primary Examiner*—Alan L. Rotman
*Assistant Examiner*—Natalia Harkaway
*Attorney, Agent, or Firm*—Gerald D. Sharkin; Richard E. Vila; Joseph J. Borovian

[57] ABSTRACT

Anti-diabetic agents of the formula:

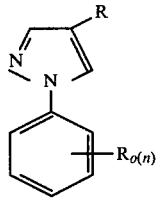

wherein
R is CHO or COOR$_1$, where R$_1$ is hydrogen or C$_{1-6}$ alkyl,
R$_o$ is C$_{1-4}$ alkyl, C$_{1-4}$ alkoxy, bromo, chloro, fluoro, trifluoromethyl, nitro or

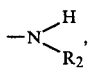

where
R$_2$ is hydrogen or C$_{1-4}$ alkyl, and
n is 0 or 1,
and the non-toxic, pharmaceutically acceptable salts thereof.

4 Claims, No Drawings

1-PHENYL-PYRAZOLE DERIVATIVES

The present invention relates to certain 1-phenyl-pyrazole derivatives, pharmaceutically acceptable salts thereof, where such may exist, and to their use as antidiabetic agents. The invention also relates to pharmaceutical compositions containing said 1-phenyl-pyrazole derivatives as active ingredients thereof and to the method of using such compositions for the treatment of diabetes.

The compounds 1-phenylpyrazole-4-carboxaldehyde, 1-(p-chlorophenyl)pyrazole-4-carboxaldehyde and 1-(p-methoxyphenyl)pyrazole-4-carboxaldehyde are disclosed in British Pat. No. 797,144. The compound 1-phenyl-pyrazole-4-carboxylic acid is disclosed in J. Chem. Soc. (1957), pp. 3314–15. The compound 1-phenyl-4-carbethoxypyrazole is disclosed in J. Am. Chem. Soc. 56, pp. 222–5 (1934). To my knowledge, no pharmacological activity has been heretofore associated with any of these compounds.

One aspect of the present invention involves the novel compositions and use of the compounds of formula I:

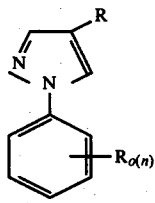
(I)

wherein
R is CHO or COOR$_1$, where R$_1$ is hydrogen or C$_{1-6}$ alkyl,
R$_0$ is C$_{1-4}$ alkyl, C$_{1-4}$ alkoxy, bromo, chloro, fluoro, trifluoromethyl, nitro or

, where
R$_2$ is hydrogen or C$_{1-4}$ alkyl, and
n is 0 or 1, or a non-toxic, pharmaceutically acceptable salt thereof.

Included among the class of compounds of formula I are the compounds of subclass Ia:

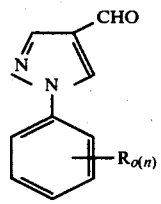
(Ia)

wherein R$_0$ and n are as defined above with respect to the compounds of formula I, or a pharmaceutically acceptable salt thereof. Preferred compounds of subclass Ia are compounds wherein R$_0$ is C$_{1-4}$ alkyl or trifluoromethyl. The more preferred compounds of subclass Ia are compounds wherein R$_0$ is trifluoromethyl. The most preferred compound of subclass Ia is 1-(m-trifluoromethylphenyl)pyrazole-4-carboxaldehyde.

Also included among the class of compounds of formula I are the compounds of subclass Ib:

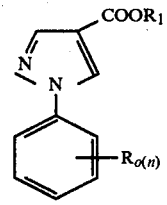
(Ib)

wherein R$_1$, R$_0$ and n are as defined above with respect to the compounds of formula I, or a pharmaceutically acceptable salt thereof. Preferred compounds of subclass Ib are compounds wherein R$_1$ is hydrogen and R$_0$ is trifluoromethyl, or a pharmaceutically acceptable salt thereof. The most preferred compound of subclass Ib is 1-(m-trifluoromethylphenyl)pyrazole-4-carboxylic acid.

Another aspect of the present invention involves the novel compounds of formula I':

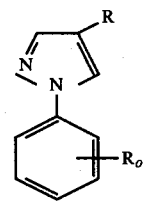
(I')

wherein
R is CHO or COOR$_1$, where R$_1$ is hydrogen or C$_{1-6}$ alkyl, and
R$_0$ is C$_{1-4}$ alkyl, C$_{1-4}$ alkoxy, bromo, chloro, fluoro, trifluoromethyl, nitro or

, where
R$_2$ is hydrogen or C$_{1-4}$ alkyl, or a non-toxic, pharmaceutically acceptable salt thereof, with the proviso that when R is CHO, R$_0$ is other than chloro or methoxy.

Preferred compounds of formula I' are the compounds of formula I":

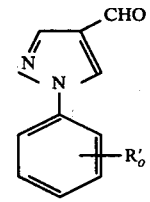
(I")

wherein R$_0$' is C$_{1-4}$ alkyl or trifluoromethyl.
The more preferred compounds of formula I" are those wherein R$_0$' is trifluoromethyl.
The most preferred compound of formula I" is 1-(m-trifluoromethylphenyl)pyrazole-4-carboxaldehyde.

Further preferred compounds of formula I′ are the compounds of formula I′″:

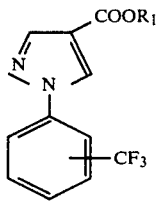  (I′″)

wherein $R_1$ is hydrogen or $C_{1-6}$ alkyl, or a pharmaceutically acceptable salt thereof.

The more preferred compounds of formula I″ are those wherein $R_1$ is hydrogen, or a pharmaceutically acceptable salt thereof.

The most preferred compound of formula I″ is 1-(m-trifluoromethylphenyl)pyrazole-4-carboxylic acid.

The compounds of subclass Ia may be prepared by subjecting a 1-phenylpyrazole compound of formula II:

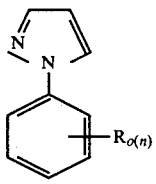  (II)

wherein $R_0$ and n are as defined above with respect to the compounds of formula I, to a conventional two-step Vilsmeier reaction. Thus, in a first step, dimethyl formamide or N-methyl formanilide, preferably dimethyl formamide, is reacted with phosphorus oxychloride at a temperature of between −20° C. and 30° C. for a period of time sufficient to allow the development of a bright red color (an indication that the reaction is complete). The resultant product is then reacted in a second step with a compound of formula II, as described above, to obtain the desired compound of subclass Ia. The second step is conveniently carried out at an initial temperature of between 30° and 80° C. and, as the reaction progresses, the temperature of the reaction is increased to 100° C. and maintained until the reaction is complete. Reaction times will, of course, vary but it is preferred that the reaction be conducted between a period of 12 and 24 hours, more preferably, between 16 and 18 hours. It will be noted that certain of the above-described compounds of subclass Ia, i.e., compounds wherein $R_0$ is

wherein $R_2$ is as defined above, can form pharmaceutically acceptable acid addition salts; it being understood that such salts are comprehended as being included within the scope of the present invention.

The compounds of subclass Ib wherein $R_1$ is hydrogen may be prepared by oxidizing a compound of subclass Ia by processes known per se for the oxidation of aldehydes. For example, the oxidation may be conducted employing the well-known Oppenauer reaction or the Jones reagent. When employing the Jones reagent, the oxidation is conveniently conducted at a temperature between 0° C. and 35° C., preferably between 0° C. and 15° C., in a suitable solvent, e.g., acetone.

It should be noted that the above-described compounds of subclass Ib bear a carboxylic acid group, and can, therefore, form pharmaceutically acceptable simple salts under mild, basic conditions, suitably employing an alkali metal hydroxide, preferably, sodium hydroxide; it being understood that such salts are intended to be embraced by the present invention. In addition, certain of the above-described compounds of subclass Ib, i.e., compounds wherein $R_0$ is

where $R_2$ is as defined above, can form pharmaceutically acceptable acid addition salts instead; it being understood that either of such salts are included within the scope of the present invention.

The compounds of subclass Ib wherein $R_1$ is $C_{1-6}$ alkyl may be prepared by esterifying a compound of subclass Ib wherein $R_1$ is hydrogen by reaction with an alcohol, i.e., a compound of formula III:

$$HO-R_1 \quad (III)$$

wherein $R_1$ is $C_{1-6}$ alkyl, under conditions conventionally employed in esterifying a carboxylic acid function. The esterification may conveniently be carried out in an inert organic solvent, for example, an aromatic hydrocarbon such as toluene, benzene or xylene, in the presence of an acidic catalyst such as an aromatic sulfonic acid, e.g., p-toluene sulfonic acid, at elevated temperatures, e.g., from 100° to 200° C., under conditions in which water formed in the reaction is removed from the system, e.g., by carrying out the esterification in an extractor apparatus charged with a drying agent. It is particularly convenient to carry out the esterification at the reflux temperature of the reaction mixture, when such falls within a suitable range. Reaction times will, of course, vary with the nature of the reactants and the reaction conditions employed, but it is preferred to carry out the reaction at more moderate temperatures, e.g., at from about 120° to 150° C. over an extended period of time, e.g., for from about 1 to 20 days.

The products of the above-described reactions may be recovered and refined in conventional manner, e.g., by crystallization, distillation or chromatographic techniques, such as eluting from a chromatographic column or separating on a silica layer.

Many of the compounds of formulae II and III are either known and obtained by methods described in the literature, or where not known, may be obtained by methods analogous to those described in the literature.

As previously indicated, pharmaceutically acceptable acid addition salts (i.e., those salts which do not significantly increase the toxicity of the basic compound) of the compounds of formula Ia and Ib, where such may exist, are included within the scope of this invention. Included are salts with inorganic acids, e.g., the hydrochloride, hydrobromide, hydroiodide, phosphate (including hydrogen phosphate), metaphosphate, sulfate (including hydrogen sulfate) and perchlorate salts.

As also previously indicated, pharmaceutically acceptable simple salts of certain of the compounds of formula Ib are included within the scope of this invention. Included are salts wherein the cation is selected from the group consisting of alkali metal, alkaline earth metal, ammonium, mono-, di- and trialkanol ammonium wherein the alkanol group contains 2 to 4 carbon atoms and mono-, di- and tri- and tetraalkylammonium wherein the alkyl group contains 1 to 4 carbon atoms. Preferred cations are those selected from the alkali metals and the alkaline earth metals. The more preferred cations are those selected from the alkali metals, most preferably, sodium and potassium.

The compounds of formula I, and their pharmaceutically acceptable salts, are useful in the treatment of diabetes as indicated in groups of six mice fasted overnight and then given orally 12.5 to 200 milligrams per kilogram of animal body weight of test compound suspended in 1.5% carboxymethyl cellulose (CMC) solution in water (Test A). Two hours after the compound is administered, the mice are anesthetized with ether and whole blood is collected via cardiac puncture. Pooled blood samples are suspended in 1.5% carboxymethyl cellulose (CMC) solution in water for assay by the Technicon Autoanalyzer potassium ferric-cyanide method #N-2b for glucose which is compared with the glucose levels for control animals treated only with 1.5% CMC solution.

The compounds of formula I, and their pharmaceutically acceptable salts, are also useful in the treatment of juvenile diabetes as indicated in mice given 175 milligrams per kilogram of body weight of streptozotocin in pH 4.5 citrate buffer to induce a juvenile type form of diabetes (Test B). The streptozotocin pretreated mice are kept in clean cages with food and water for 6 days, and those mice that show a positive urine clinistix reaction at the end of 6 days are considered diabetic. These mice are given 50 to 200 milligrams per kilogram of animal body weight of test compound while at the same time all food is removed from the cages. Two hours after the compound is administered, the mice are anesthetized with ether and whole blood is collected via cardiac puncture. The blood is placed in autoanalyzer cups containing 0.025 cc. of heparin 1000 units/ml. and the samples are capped, shaken, and kept in ice buckets until analyzed for glucose. The glucose level is determined by the autoanalyzer potassium ferric-cyanide method #N-2b and compared with control animals treated only with the streptozotocin in citrate buffer.

The compounds are particularly useful in the treatment of mature onset diabetes.

For anti-diabetic use, the compounds of formula I and their non-toxic, pharmaceutically acceptable salts may be administered orally or parenterally as such or admixed with conventional pharmaceutical carriers. They may be administered orally in such forms as tablets, dispersible powders, granules, capsules, syrups and elixirs, and parenterally as solutions, e.g., a sterile injectable aqueous solution. The compositions for oral use may contain one of more conventional adjuvants, such as sweetening agents, flavoring agents, coloring agents and preserving agents, in order to provide an elegant and palatable preparation. Tablets may contain the active ingredient in admixture with conventional pharmaceutically acceptable excipients, e.g., inert diluents, such as calcium carbonate, sodium carbonate, lactose, and talc, granulating and disintegrating agents, e.g. starch and alginic acid, binding agents, e.g., starch, gelatin and acacia, and lubricating agents, e.g., magnesium stearate, stearic acid and talc. The tablets may be uncoated or coated by known techniques to delay disintegration and adsorption in the gastrointestinal tract and thereby provide a sustained action over a longer period. Similarly, suspensions, syrups and elixirs may contain the active ingredient in admixture with any of the conventional excipients utilized in the preparation of such compositions, e.g., suspending agents such as methylcellulose, tragacanth and sodium alginate; wetting agents such as lecithin, polyoxyethylene stearate and polyoxyethylene sorbitan monooleate; and preservatives such as ethyl-p-hydroxybenzoate. Capsules may contain the active ingredient alone or admixed with an inert solid diluent, e.g., calcium carbonate, calcium phosphate and kaolin. The injectable compositions are formulated as known in the art. These pharmaceutical preparations may contain up to about 90% of the active ingredient in combination with the carrier or adjuvant.

The anti-diabetic effective amount of active ingredient employed in the treatment of diabetes may vary depending on the particular compound employed, the mode of administration and the severity of the condition being treated. However, in general, satisfactory results in the treatment of diabetes are obtained when a compound of formula I, or a pharmaceutically acceptable salt thereof, is administered at a daily dosage of from about 5 milligrams to about 300 milligrams per kilogram of animal body weight, preferably given orally and in divided doses two to four times a day, or in sustained release form. For most large mammals, the total daily dosage is from about 350 milligrams to about 3000 milligrams. Unit dosage forms suitable for internal use comprise from about 50 milligrams to about 3000 milligrams, more usually 50 to 1500 milligrams, of the active compound in intimate admixture with a solid or liquid, pharmaceutically acceptable carrier.

Tablets and capsules containing the ingredients indicated below may be prepared by conventional techniques and are useful in treating diabetes, particularly mature onset diabetes, at a dose of one tablet or capsule, 2 to 4 times a day.

|  | Weight (mg.) | |
| --- | --- | --- |
| Ingredients | tablet | capsule |
| 1-(m-trifluoromethylphenyl)-pyrazole-4-carboxylic acid | 100 | 100 |
| tragacanth | 10 | — |
| lactose | 247.5 | 300 |
| corn starch | 25 | — |
| talcum | 15 | — |
| magnesium stearate | 2.5 | — |
| Total | 400.0 | 400 |

The following pharmaceutical compositions are formulated with the indicated amount of active ingredient using conventional techniques. The injectable suspension and the oral liquid suspension represent formulations useful as unit doses and may be administered in the treatment of diabetes, particularly mature onset diabetes. The injectable suspension is suitable for administration once or twice a day whereas the oral liquid suspension is suitable administered 2 to 4 times a day.

|  | Weight (mg.) | |
| --- | --- | --- |
| Ingredients | sterile injectable suspension | oral liquid suspension |
| 1-(m-trifluoromethylphenyl)-pyrazole-4-carboxylic acid | 200 | 100 |

|  | Weight (mg.) | |
| --- | --- | --- |
| Ingredients | sterile injectable suspension | oral liquid suspension |
| sodium carboxymethylcellulose U.S.P. | 1.25 | 12.5 |
| methyl cellulose | 0.4 | — |
| polyvinylpyrrolidone | 5 | — |
| lecithin | 3 | — |
| benzyl alcohol | 0.01 | — |
| magnesium aluminum silicate | — | 47.5 |
| flavor | — | q.s. |
| color | — | q.s. |
| methyl paraben, U.S.P. | — | 4.5 |
| propyl paraben, U.S.P. | — | 1.0 |
| polysorbate 80 (e.g., Tween 80), U.S.P. | — | 5 |
| sorbitol solution, 70%, U.S.P. | — | 2,500 |
| buffer agent to adjust pH for desired stability | q.s. | q.s. |
| water | for injection, q.s. to 1 ml. | q.s. to 5 ml. |

The preferred pharmaceutical compositions from the standpoint of preparation and ease of administration are solid compositions, particularly liquid or hard-filled capsules and tablets containing from about 100 to 200 milligrams of the active ingredient.

The following examples are merely illustrative of representative compounds encompassed by this invention and their synthesis and are not intended as in any way limiting the scope of the invention.

EXAMPLE 1

1-(m-trifluoromethylphenyl)pyrazole-4-carboxaldehyde

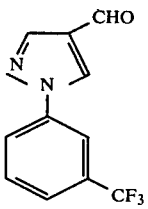

Into a 500 ml., 2-neck flask, fitted with a condenser and a magnetic stirrer, containing 60.5 ml. (0.78 M.) of absolute dimethylformamide (dried over 3A sieves) is slowly added, while the temperature is maintained at less than 10° C., 36.9 ml. (0.39 M.) of phosphorus oxychloride, after which time the reaction mixture is allowed to stand at room temperature until a bright red color develops (typically, between 30 and 60 minutes). To the resultant reaction mixture is then added 23.2 g. (0.109 M.) of 1-(m-trifluoromethylphenyl)-pyrazole, while the temperature is maintained at between 50° and 70° C. The reaction mixture is then slowly heated to 100° C. and allowed to stand overnight, while the temperature is maintained at 100° C. The reaction mixture is then cooled, quenched in ice water and allowed to stand overnight at room temperature. The resultant precipitated solids are then filtered and washed successively with water and petroleum ether. The solvent is then removed under vacuum to yield 1-(m-trifluoromethylphenyl)pyrazole-4-carboxaldehyde (Yield: 57%). A second crop was also obtained, m.p. 80°-82° C. (Yield: 63%).

Test A: $ED_{25}$-79.2 mg./kg.

EXAMPLE 2

Following essentially the procedure of Example 1, and using in place of 1-(m-trifluoromethylphenyl)-pyrazole, an equivalent amount of:

(a) 1-phenyl-pyrazole,
(b) 1-o-tolyl-1H-pyrazole,
(c) 1-(o-nitrophenyl)-pyrazole, or
(d) 1-(p-chlorophenyl)-pyrazole,
there is obtained
(a) 1-phenylpyrazole-4-carboxaldehyde,
(b) 1-(o-tolyl)pyrazole-4-carboxaldehyde, m.p. 54°-56° C., Test A: $ED_{25}$-34 mg./kg.
(c) 1-(o-nitrophenyl)pyrazole-4-carboxaldehyde, and
(d) 1-(p-chlorophenyl)pyrazole-4-carboxaldehyde, respectively.

EXAMPLE 3

1-(m-trifluoromethylphenyl)pyrazole-4-carboxylic acid

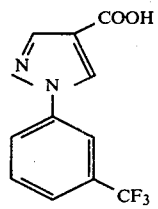

Into a 500 ml. Erlenmeyer flask, fitted with a thermometer and a magnetic stirrer, containing a solution of 8.3 g. (0.0346 M.) of 1-(m-trifluoromethylphenyl)-pyrazole-4-carboxaldehyde in 300 ml. of acetone is slowly added 20.0 ml. of Jones reagent (prepared by dissolving 26.7 g. of chromium trioxide in 23.0 ml. of concentrated sulfuric acid and then diluting to 100 ml. with water), the addition of the Jones reagent being effected while the solution is cooled by an ice water bath. Upon completion of the addition of the Jones reagent, the reaction mixture is stirred, under cooling, for 15 minutes and then for an additional 20 minutes at room temperature, after which time it is quenched with a large volume of water and allowed to stand at room temperature for about 3 hours. The resultant precipitated solids are then filtered and washed successively with water and petroleum ether. The solvent is then removed under vacuum to yield 1-(m-trifluoromethylphenyl)pyrazole-4-carboxylic acid, m.p. 145°-148° C. (Yield: 89%).

Test A: $ED_{25}$-43 mg./kg.

EXAMPLE 4

Following essentially the procedure of Example 3, and using in place of 1-(m-trifluoromethylphenyl)-pyrazole-4-carboxaldehyde, an equivalent amount of each of the compounds produced in Example 2, there is obtained:

(a) 1-phenylpyrazole-4-carboxylic acid,
(b) 1-(o-tolyl)pyrazole-4-carboxylic acid, m.p. 105°-107° C., Test A: $ED_{25}$-19.1 mg./kg.
(c) 1-(o-nitrophenyl)pyrazole-4-carboxylic acid, and
(d) 1-(p-chlorophenyl)pyrazole-4-carboxylic acid, respectively.

What is claimed is:

1. A compound of formula I':

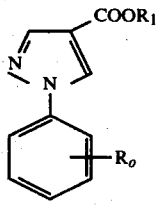 (I')

wherein
  $R_1$ is hydrogen or $C_{1-6}$ alkyl, and
  $R_0$ is $C_{1-4}$ alkoxy, bromo, chloro, fluoro, trifluoromethyl or

, where $R_2$ is hydrogen or $C_{1-4}$ alkyl, or a pharmaceutically acceptable simple or acid addition salt thereof.

2. A compound according to claim 1 of formula I''':

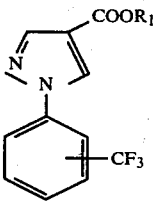 (I''')

wherein $R_1$ is hydrogen or $C_{1-6}$ alkyl, or a pharmaceutically acceptable salt thereof.

3. A compound according to claim 2 wherein $R_1$ is hydrogen, or a pharmaceutically acceptable salt thereof.

4. A compound of claim 3 which is 1-(m-trifluoromethylphenyl)pyrazole-4-carboxylic acid.

* * * * *

UNITED STATES PATENT AND TRADEMARK OFFICE
CERTIFICATE OF CORRECTION

PATENT NO. : 4,220,792
DATED : September 2, 1980
INVENTOR(S) : Paul L. Anderson/Nicholas A. Paolella It is certified that error appears in the above—identified patent and that said Letters Patent is hereby corrected as shown below:

Column 3, lines 3 and 6 beneath the first structural formula; delete "I"" and insert in its place --I"--.

Column 6, line 61; delete "suitable" and insert in its place --suitably--.

Signed and Sealed this

Sixth Day of October 198.

|SEAL|

Attest:

Attesting Officer

GERALD J. MOSSINGHOFF
Commissioner of Patents and Trademarks